United States Patent
Freifeld et al.

(10) Patent No.: US 7,082,185 B2
(45) Date of Patent: Jul. 25, 2006

(54) PORTABLE IMAGING SYSTEM METHOD AND APPARATUS

(75) Inventors: Barry M. Freifeld, Oakland, CA (US); Timothy J. Kneafsley, Albany, CA (US); Jacob Pruess, Berkeley, CA (US); Liviu Tomutsa, Hercules, CA (US); Paul A. Reiter, Berkeley, CA (US); Ted M. deCastro, Castro Valley, CA (US)

(73) Assignee: The Regents of the University of California, Oakland, CA (US)

( * ) Notice: Subject to any disclaimer, the term of this patent is extended or adjusted under 35 U.S.C. 154(b) by 157 days.

(21) Appl. No.: 10/777,947

(22) Filed: Feb. 11, 2004

(65) Prior Publication Data

US 2004/0218716 A1 Nov. 4, 2004

Related U.S. Application Data

(60) Provisional application No. 60/447,496, filed on Feb. 12, 2003.

(51) Int. Cl.
- G01N 23/069 (2006.01)
- G01N 23/04 (2006.01)
- H05G 1/00 (2006.01)
- G01V 5/00 (2006.01)

(52) U.S. Cl. .......................... 378/53; 378/62; 378/208; 250/255

(58) Field of Classification Search ............ 378/53–59, 378/37, 62, 102, 203, 208; 73/152.11; 250/253, 250/255, 505.1
See application file for complete search history.

(56) References Cited

U.S. PATENT DOCUMENTS

| | | | | |
|---|---|---|---|---|
| 4,020,346 A | * | 4/1977 | Dennis | 378/57 |
| 4,977,585 A | * | 12/1990 | Boyd | 378/4 |
| 4,977,586 A | | 12/1990 | Curry | |
| 5,153,899 A | | 10/1992 | Curry | |
| 5,712,893 A | * | 1/1998 | Dykster et al. | 378/58 |
| 6,275,563 B1 | | 8/2001 | Griffin, Jr. | |
| 6,325,538 B1 | * | 12/2001 | Heesch | 378/203 |
| 6,389,101 B1 | * | 5/2002 | Levine et al. | 378/85 |
| 6,448,571 B1 | * | 9/2002 | Goldstein | 250/515.1 |
| 6,526,120 B1 | * | 2/2003 | Gray et al. | 378/57 |
| 6,935,779 B1 | * | 8/2005 | Zhang et al. | 378/207 |

\* cited by examiner

*Primary Examiner*—Edward J. Glick
*Assistant Examiner*—Irakli Kiknadze
(74) *Attorney, Agent, or Firm*—Joseph R. Milner

(57) ABSTRACT

An operator shielded X-ray imaging system has sufficiently low mass (less than 300 kg) and is compact enough to enable portability by reducing operator shielding requirements to a minimum shielded volume. The resultant shielded volume may require a relatively small mass of shielding in addition to the already integrally shielded X-ray source, intensifier, and detector. The system is suitable for portable imaging of well cores at remotely located well drilling sites. The system accommodates either small samples, or small cross-sectioned objects of unlimited length. By rotating samples relative to the imaging device, the information required for computer aided tomographic reconstruction may be obtained. By further translating the samples relative to the imaging system, fully three dimensional (3D) tomographic reconstructions may be obtained of samples having arbitrary length.

33 Claims, 3 Drawing Sheets

PORTABLE IMAGING SYSTEM METHOD AND APPARATUS

STATEMENT REGARDING FEDERAL FUNDING

This invention was made with U.S. Government support under Contract Number DE-AC03-76SF00098 between the U.S. Department of Energy and The Regents of the University of California for the management and operation of the Lawrence Berkeley National Laboratory. The U.S. Government has certain rights in this invention.

CROSS REFERENCE TO RELATED APPLICATIONS

This application takes priority of U.S. Provisional Patent application No. 60/447,496 filed Feb. 12, 2003, and entitled "Portable Imaging System Method and Apparatus", which is hereby incorporated by reference.

REFERENCE TO A COMPUTER PROGRAM

Not Applicable.

BACKGROUND OF THE INVENTION

1. Field of the Invention

The present invention pertains generally to portable imaging devices; more particularly to portable scanning or computer assisted tomographic imaging using ionizing radiation; and yet more particularly to portable X-ray imaging of drilling core samples.

2. Description of the Relevant Art

U.S. Pat. Nos. 4,977,586 and 5,153,899, both by the same inventor, both entitled "Portable Tire X-ray Apparatus and Method," and both hereby incorporated by reference, disclose methods and devices for radiographically imaging tires using an X-ray viewing apparatus. However, both systems disclose operator shielding, which is accomplished by using a "trailer" to contain spurious X-ray emissions, and thereby protect operators from excessive X-ray doses from the X-ray imaging apparatus.

U.S. Pat. No. 6,275,563, entitled "Portable Gamma Apparatus for Core Analysis and Method Therefor", incorporated herein by reference, discloses a gamma ray (γ-ray) imaging device for radiographically examining well cores. However, in this apparatus, the lead shielding disclosed is used solely to reduce the background radiation from producing noise in the γ-ray scintillator used for detecting γ-rays transmitted through a well bore core sample, and fails to teach operator radiation exposure mitigation by radiation shielding of any sort.

BRIEF SUMMARY OF THE INVENTION

In one embodiment, this invention provides for an X-ray imaging device useful for imaging an object contained within an X-ray shielded volume comprising: an X-ray source; an X-ray imaging detector; and an X-ray shielded volume comprising: i) a core volume and a beam path within a beam path volume, and ii) said beam path volume intersecting said core volume; wherein said X-ray source is located at one end of said beam path, and said X-ray imaging detector is located at another end of said beam path so as to image an object placed in said beam path.

In another embodiment, this invention provides for an X-ray imaging device for imaging a sample contained within an X-ray shielded volume comprising: an X-ray source capable of emitting an X-ray beam within a beam path to illuminate a sample; an X-ray imaging detector; and an X-ray shielded volume comprising: a left volume shield and a right volume shield separably connected so as to permit insertion and removal of said sample, wherein, when said left volume shield and said right volume shield are connected, any gap between any of the elements of said X-ray imaging device emits X-ray photons at a level equal to or below a regulatory level; wherein said beam path is capable of illuminating said sample to produce an image on said X-ray imaging detector; wherein said X-ray source, said X-ray imaging detector, and said X-ray shielded volume have sufficient optical depth to limit the transmitted X-ray photons at a level equal to or below said regulatory level; and wherein, when said left volume shield and said right volume shield are connected enclosing said sample, any gap between any of the elements of said X-ray imaging device and said sample emits X-ray photons at a level equal to or below said regulatory level.

In still another embodiment, this invention provides for an X-ray imaging device for imaging a sample contained within an X-ray shielded volume comprising: an X-ray source; an X-ray imaging detector comprising: an X-ray image intensifier, and an image detector that detects the output of said X-ray image intensifier; and an X-ray shielded volume comprising: a core volume shielded by a left volume shield and a right volume shield separably connected so as to permit insertion and removal of a sample, said core volume having a top opening and a bottom opening, a beam path emitted within a beam path volume, a shielded telescoping sleeve permitting elongation of said beam path volume, said beam path volume intersecting said core volume; wherein said X-ray source is located at one end of said beam path, and said X-ray imaging detector is located at another end of said beam path so as to image an object placed in said beam path; and wherein said X-ray source is shielded from externally radiating substantial radiation by said X-ray shielded volume.

BRIEF DESCRIPTION OF THE SEVERAL VIEWS OF THE DRAWINGS

The invention will be more fully understood by reference to the following drawings, which are for illustrative purposes.

DETAILED DESCRIPTION OF THE PREFERRED EMBODIMENT

X-Ray Core Imaging

Figure 1A:
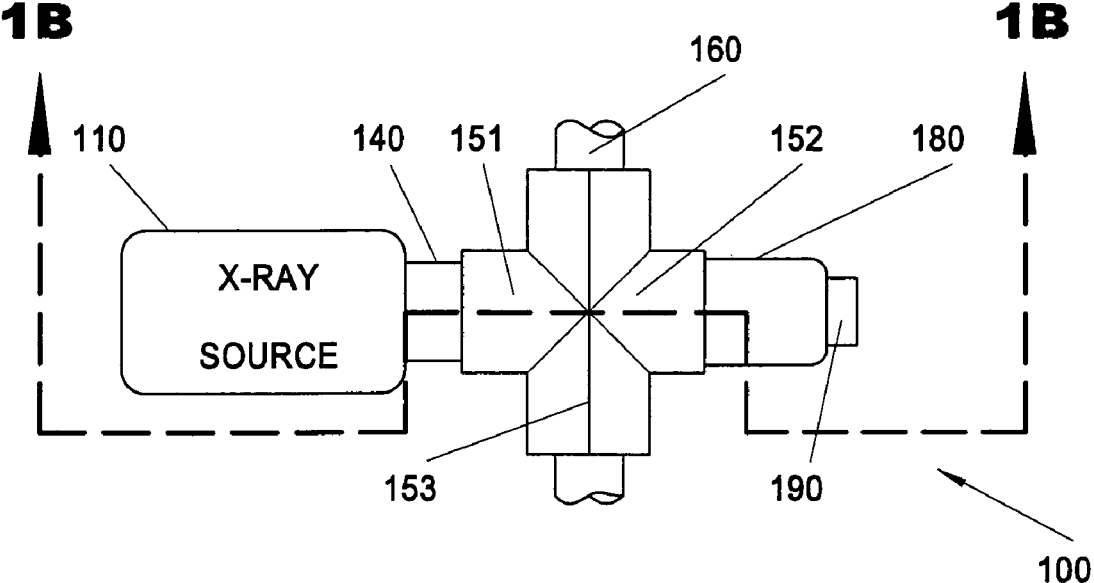
FIG. 1A is a side view of the X-ray imaging device.

When wells are drilled with an open cylindrical boring bit, cores may be produced that contain the contents of the geological strata (or layers) of the drilled path. By determining the composition and physical properties of these cores, assessments may be made of the economic viability of producing oil and/or natural gas from the well and associated well field. X-ray imaging of geological cores provides details on the macroporous core structure, which is important in assessing the potential for extracting recoverable resources. X-ray imaging may be coupled with additional measurement techniques, such as miscible and immiscible fluid displacement test results, that may provide added information on the core's physical properties by visualizing transport processes within the recovered core.

Naturally occurring methane hydrate can be recovered in drilled well cores. However, methane hydrate is unstable at standard temperature and pressure, and as such, it usually rapidly decomposes soon after it is retrieved from such cores. At standard temperature and pressure methane hydrate transforms into either liquid or ice, while evolving free methane gas.

One method used to determine the presence of methane hydrate and its spatial distribution in the well core is by allowing the decomposition of the methane hydrate-containing sample while imaging the sample. By collecting a time series of X-ray images during the methane hydrate decomposition, the distribution of methane hydrate can be determined by observing reductions in X-ray attenuation as methane gas is permitted to outgas. This method is further addressed in the conference paper "X-ray computed tomography observation of methane hydrate dissociation," Society of Petroleum Engineers report SPE 75533, delivered at the 2002 SPE Gas Technology Symposium, and incorporated herein by reference.

To address the problem of identifying the presence of methane hydrate and its room temperature instability in recovered drill cores there are generally two alternate solutions. A first, and most typically used method is to preserve the samples within a stable portion of the pressure-temperature phase diagram regime where methane hydrate is solid, either by: 1) using quick refrigeration of core samples to temperatures at or below about 77° K (the temperature of liquid nitrogen at standard atmospheric pressure), or 2) greatly increasing the pressure at which the core samples are stored at room temperature. Other pressure-temperature combinations using both low temperatures and high pressures can also maintain the methane hydrate at a thermodynamically stable state within the solid phase portion of the methane hydrate pressure-temperature phase diagram.

The refrigeration method described above is expensive due to the costs of maintaining a plethora of typically bulky core samples at this low temperature until analysis can be performed, as well as transportation costs incurred by moving the core samples from the well drilling site, to the low temperature storage location, to an analytical laboratory, and again back to storage, all the while maintaining the low temperature. Conversely, transporting samples at high pressures is also expensive and requires the use of high-pressure vessels, which may be subject to various transportation and safety regulations. Any method that transports the samples must additionally address the potential accidental evolution and release of flammable methane gas from the methane hydrate, and potential liability thereof.

A second method used to determine the presence of methane hydrate and its spatial distribution in the well core is to analyze the core samples as they are extracted from the well, prior to the heat-induced (albeit typically only room temperature) breakdown and decomposition of the methane hydrate. This method has not typically been used since it involves moving a large screened X-ray system from well drilling location to location.

Traditional X-ray systems have very large masses to adequately shield people from the generated X-ray radiation used in X-ray imaging. Since the shielded rooms have a very large surface area, and since the shielding weight is proportional to the surface area, the resultant shielded X-ray imaging systems are bulky and very heavy. These limitations practically result in this second method only being used very infrequently.

In one embodiment of the invention, a preferable X-ray is generated by a 10–200 kV X-ray generator, manufactured by Thermo Electron Corp., Thermo NORAN/Thermo Kevex X-Ray, Scotts Valley, Calif. as the PXS10–65W. Alternative photon sources may also include $\gamma$-ray sources. The preferably image intensifier is the PT62VHRC operating with model PVCCDS6.5SPCL, both manufactured by Precise Optics/PME, Inc. of Bay Shore, N.Y.

Although all of the imaging discussed thus far has used as an example X-ray photons, any penetrative high-energy photon may be used so long as a suitable detector may be used for imaging the transmitted and scattered photons. Alternative sources would be sources with 10–130 kV, 20–130 kV, or 70–80 kV generation voltages.

Operator X-Ray Irradiation

All X-ray imaging systems produce unintended emissions to operators in proximity to the systems through scatter, transmission, and leakage. Typically, these emission levels are very low, and for extremely well shielded applications, may not even be detectable with common instrumentation. Typically, portable X-ray systems are of a "cabinet" design. A cabinet X-ray system is one where the source, target, and associated equipment are contained within a cabinet. Various regulatory agencies have determined that some X-ray exposure is acceptable, according to the energy levels and time durations to which an operator is exposed. In the United States of America, 21 CFR §1020.40(c)(1)(i) provides a regulatory standard for cabinet X-ray systems where an emission limit is established specifying that:

"[r]adiation emitted from the cabinet [X]-ray system shall not exceed an exposure of 0.5 milliroentgen in one hour at any point 5 centimeters outside the external surface."

21 CFR §1020.40(c)(4)(i) imposes further standards for interlock safety that does not permit operation of the X-ray source at times when an operator can be exposed to the beam path:

"Each door of a cabinet [X]-ray system shall have a minimum of two safety interlocks. One, but not both of the required interlocks shall be such that door opening results in physical disconnection of the energy supply circuit to the high-voltage generator, and such disconnection shall not be dependent upon any moving part other than the door."

Any commercially practicable portable imaging device must meet these regulatory requirements in the United States of America. The most difficult requirement is typically the "0.5 milliroentgen in one hour at any point 5 centimeters outside the external surface." It is likely that analogous international requirements exist for operator X-ray exposure protection.

Portable X-Ray Imaging

The invention described here addresses the shielding requirements of an X-ray imaging system so as to reduce the X-ray shielded volume and consequent surface area of the of shielding, which thereby reduces the weight of the overall imaging system. One advantage of reducing the weight is that cost of the X-ray shielding is reduced by reduction of the shielded surface area. However, perhaps the biggest advantage is that the system becomes much more portable since it is smaller and lighter.

Important to system portability is reducing the X-ray shielded volume to a minimum commensurate with the particular application. Of particular interest here are X-ray core imaging, and protection of X-ray irradiation of operators as described above. By reducing the X-ray shielded volume, the shielding surface area, and hence system weight, is minimized. Reducing both size and weight contribute to making a more easily portable system.

Figure 1B:
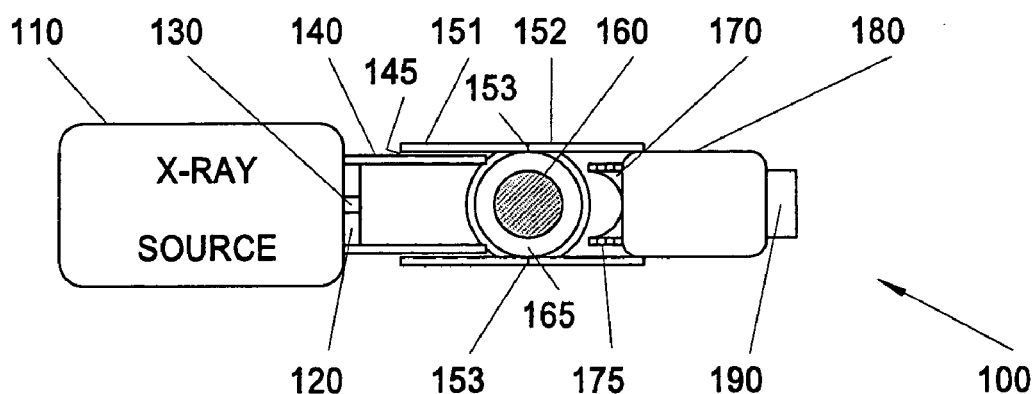
FIG. 1B is a partial cross-sectional view of the X-ray imaging device with a portion of the detailed internal structure depicted.

Refer now to FIG. 1A and FIG. 1B. FIG. 1A is a side view of an imaging system 100. FIG. 1B is a corresponding partial cross section of FIG. 1A. An X-ray source 110 is partially collimated by a beam block 120, which in turn has an aperture 130. Beam block 120 may be attached or removably attached either to X-ray source 110, or X-ray source shield 140. The X-ray beam (subsequently shown in FIGS. 1C and 1E as cross sections of the beam volume 150) exits the aperture 130, where it is shielded from the operator by X-ray source shield 140, which is attached to the X-ray source 110. The X-ray source 110, beam block 120, and X-ray source shield 140, can translate as a unit toward and away from the core sample 160. In this translation to achieve optimal core sample 160 X-ray illumination, X-rays will not have a line-of-sight or scattering path exit from the slight gap 145 formed between the X-ray source shield 140, and the beam path volume shield comprising a left volume shield 151 and a right volume shield 152 which separably meet at a labyrinth X-ray seal 153. The X-ray labyrinth seal 153 permits no greater level of X-ray transmission than the bulk shielding comprising either the X-ray source shield 140, the left volume shield 151, or the right volume shield 152. Like traditional optical light seals, there is no line-of-sight path from one side of the X-ray labyrinth seal 153 to the other.

Labyrinth seals take their name from the word "labyrinth," which is a structure from which it is very difficult to exit. Likewise, a labyrinth seal makes it very difficult for photons, in this instance, X-ray photons, to exit. Many designs may be found for such seals, which typically have a common feature that their interconnection gaps are surrounded by material making line-of-sight egress from such as gap impossible. For X-ray and other photonic purposes, scattering and reflection of photons are taken into account by requiring a photon to make sufficient turns that it has an extremely low probability of traversing the seal from one side to the other.

Figure 1C:
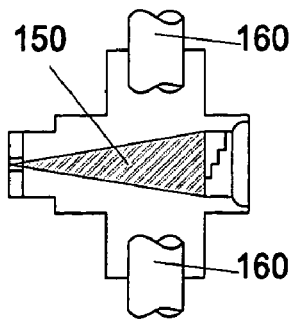
FIG. 1C is a partial side view of the X-ray imaging device showing the beam path volume.
Figure 1D:
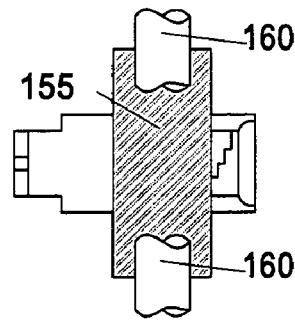
FIG. 1D is a partial side view of the X-ray imaging device showing the core volume.
Figure 1E:
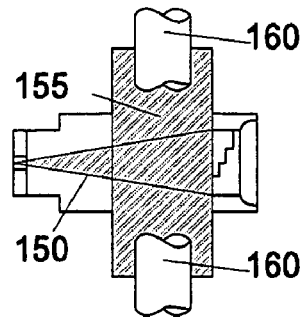
FIG. 1E is a partial side view of the X-ray imaging device showing both the beam path and core volumes.

The X-ray shielded volume (formed by the left volume shield 151 and the right volume shield 152) works with the X-ray source shield 140 to shield the region actively irradiated by the X-ray source 110. Refer now to FIGS. 1C–1E, which show the cross sections of various X-ray illuminated regions. These views are pictorial representations of a portion of FIG. 1A, highlighting the active beam areas, with the core sample 160 partially cut away for clarity. FIGS. 1C and 1E indicate the conical region of direct illumination of the beam path, which forms the illuminated beam volume 150. FIG. 1D and 1E show the region referred to as the core volume 155, which cylindrically encompasses the core sample 160 within the X-ray shielded volume and clearance for movement therebetween (nominally about 2–4 millimeters, preferably 3.2 mm). The vertical extents of the X-ray shielded volume are determined such that combined X-ray leakage rates via X-ray photonic transmission and scatter emitted between the core sample 160 gap 165 (which is greatly exaggerated for clarity) remain at or below permissible regulatory X-ray dosage levels.

The left volume shield 151 and the right volume shield 152 each comprise an elongated, convex shape for receiving an elongated, generally cylindrical sample. Other geometries can be envisioned for other shapes of samples. One volume shield (151) is connected to the X-ray source 110 through one transverse tubular opening, defined generally as shown in FIG. 1A for receiving a concentric tube connected to the X-ray source and containing the X-ray beam. Similarly, the other volume shield (152) contains a transverse tube for receiving the X-ray beam that has passed though the sample into a measuring system, in this case comprising an attenuator 170. The end of the volume shields adjacent the sample is adapted so that the edges of the transverse tubes therein may contact the sample substantially around the entire circumference of the transverse tube.

Thus, in the preferred embodiment, there is provided a pair of volume shields that are moved together to confine a sample in close proximity. That is, the inner surface of the volume shield closely approximates the outer surface of the sample. Each volume shield contains a transverse tube, which may be characterized as a tube joined to a tube. One transverse tube connects to an x-ray source, preferably (but not necessarily) through a tube attached to the x-ray source which slides in close proximity to the transverse tube, either outside or inside the transverse tube. The other transverse tube is similarly coupled to means for detecting the x-ray beam emerging from the sample.

An essential concept of the present invention is the ability to open and close the shielding around the sample, as discussed below. The shields move on an axis defined by the center of the transverse tubes to open and receive a sample and close to contain the sample. For convenience of design the transverse tubes are of the same general size and the first and second (left and right) volume shields are axially symmetrical.

Alternative geometries are available for shielding the volume enclosed by the X-ray shielded volume, and the telescoping X-ray source shield 140 are readily discernable. For instance, the circular tubular components indicated could instead have cross-sections that are elliptical or trapezoidal in shape without altering functionality.

The left volume shield 151 and the right volume shield 152 components separably open and close around core sample 160. In one embodiment of the invention, the left volume shield 151 retracts over the X-ray source shield 140. In another embodiment, the source shield 140 is removed, and the left volume shield 151 is designed to be longer, thereby connecting directly to the X-ray source 110. Similarly, the right volume shield 152 slides in the opposite direction, preferably in conjunction with an X-ray attenuator 170 (otherwise known as a compensator, as the attenuation is very nonuniform), an image intensifier 180, and an imaging device 190 (these latter three components described further below). In yet another embodiment, the left volume shield 151 and the right volume shield 152 remains in position while the core sample 160 is slid off of a bottom supporting thrust bearing and detached from mounting on a core rotation motor 240 (shown in FIG. 2). By opening these volume shields, insertion and removal of core sample 160 into the imaging system 100 is greatly facilitated. The resulting instrument has in a greatly reduced shielded volume requirement. Interlock safety switches (not shown) disposed between the left volume shield 151 and the right volume shield 152 provide a method for positive disconnection of the high voltage supply circuit from the X-ray source 110 and prevents operation of the X-ray source 110 without proper alignment of the left volume shield 151 and the right volume shield 152, thereby meeting another US regulatory requirement.

In one embodiment of the invention, the distance from the X-ray source 110 to the image intensifier 180 is a mere 43.2 cm, or 17 inches. This is turn leads to a total mass of the X-ray source shield 140, left volume shield 151, and right volume shield 152 totaling 13.64 kg, or weighing 30 pounds. In this embodiment, the overall imaging device 100 emplaced within a portable X-ray imager 200 (described later in FIG. 2) weighs approximately 650 pounds, or masses 295.5 kg. In another embodiment, the left volume shield 151 and right volume shield 152 are assembled as a unit, and the X-ray source shield 140 is omitted, resulting in even lower shielding mass.

Figure 1F:
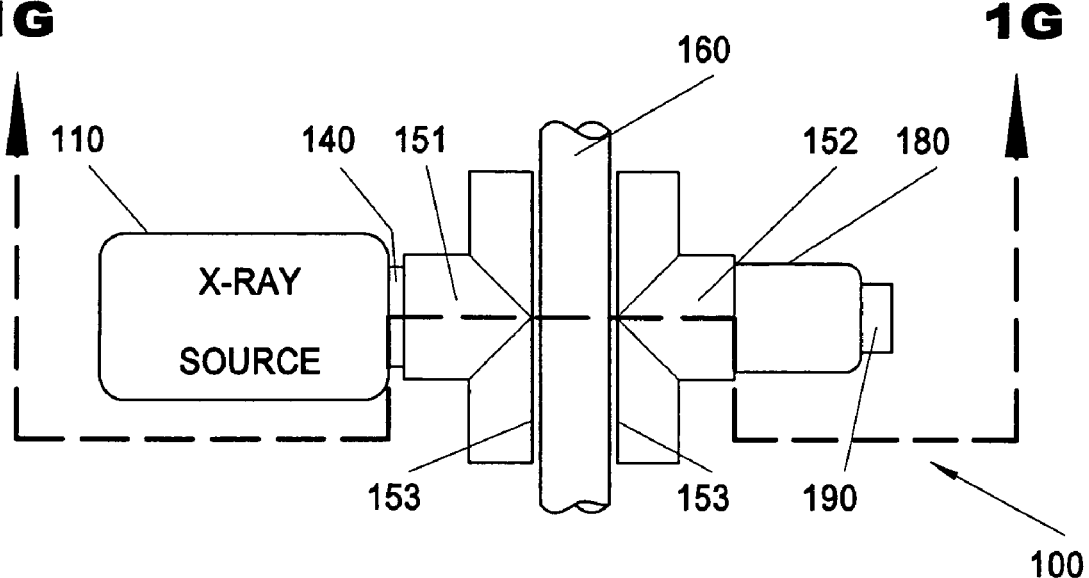
FIG. 1F is a side view of the X-ray imaging device showing the X-ray source assembly and detector assembly retracted for core installation or replacement.
Figure 1G:
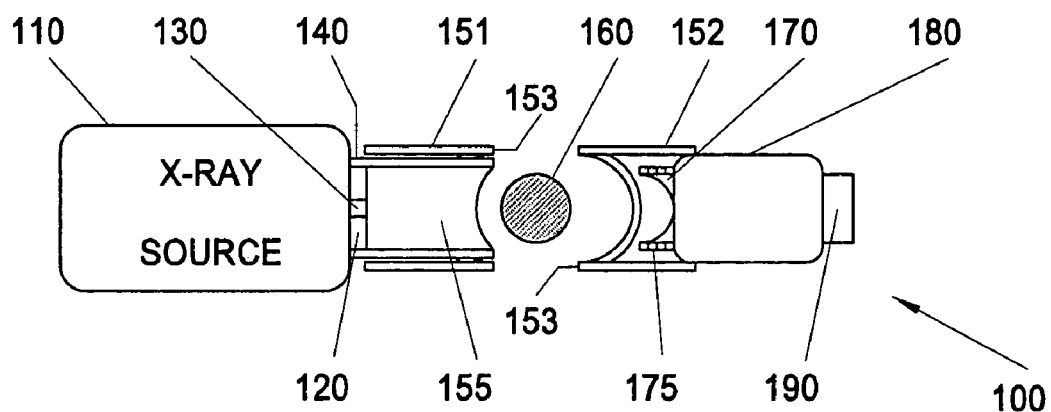
FIG. 1G is a top view of the X-ray imaging device showing the X-ray source assembly and detector assembly retracted for core installation or replacement.
Figure 1H:
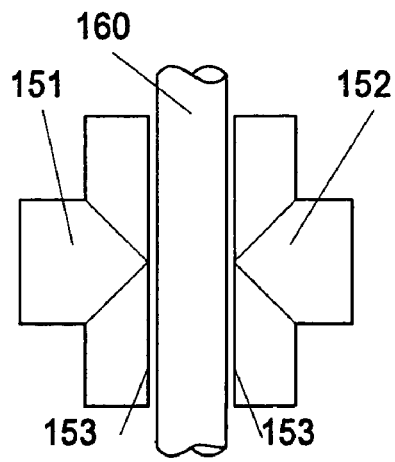
FIG. 1H is a partial side view of the X-ray imaging device showing the X-ray shielding surrounding the core volume retracted for core installation or replacement.

Referring now to FIGS. 1F, 1G and 1H, a core sample 160, preferably a well core, is placed into the opening formed by the separation of openings at both ends of the retracted left volume shield 151 and the right volume shield 152. To initiate core sample 160 analysis, the retracted left volume shield 151 and the right volume shield 152 pieces are reunited. Switches (not shown) indicate such reunion, and pass power to allow operation of the X-ray source 110.

Referring again to FIG. 1B, the assembled left volume shield 151 and the right volume shield 152 pieces form a gap 165 with the outer diameter of the core sample 160. This gap 165 (shown much larger than actual size for visual emphasis) forms a low albedo path that is sized according to principles well known to those in the art of radiation shielding so as to not permit scattered X-rays to leave the imaging system 100 at a level greater than permissible regulatory levels for operator exposure.

Refer now to FIGS. 1A–1E. The beam path 150 (FIG. 1C) begins at the X-ray source 110, passes through aperture 130, illuminates the core sample 160, and proceeds to an attenuator 170 having calibration steps 175 used in image post-processing to account for shot-to-shot X-ray beam intensity fluctuations. The beam path 150 continues to an image intensifier 180, which produces photons imaged by an imaging device 190. The imaging system, comprised of the image intensifier 180 and the imaging device 190, is a photon multiplication and counting device, used in many fields for imaging applications. The most preferable image intensifier 180 would be a micro-channel plate (MCP) type so that the position information of the incoming X-ray photons is maintained and transferred to the output of the MCP. The imaging device 190 is in turn preferably connected to a data processing device or computer system (not shown) preferably for collection and/or storage of images, and more preferably for local and/or remote computer tomography calculations to resolve a collection of rotated core sample 160 images into their corresponding internal volumetric pixels, or voxels.

The optional optical attenuator 170 is formed to reduce the dynamic range of transmitted X-rays through a circular cross-sectioned core. In one embodiment, this works well with an aluminum attenuator shaped as a rectangular block having a partial cylindrically bored section parallel to the geological core axial dimension removed. In another embodiment, the attenuator is acylindrically (a term analogously related to a cylinder as aspheric is to a sphere) designed to account for the cylindrical core sample 160 and the core sample sheath (or core holder, which is typically a plastic or aluminum tube), interacting with the X-ray beam path 150 dispersing from the X-ray source 110. The calculated shape minimizes dynamic range of the transmitted image. By forming the attenuator in this fashion, X-rays passing through a thin edge of the core sample 160, which would otherwise be quite intense, are reduced in brightness by the attenuator. By reducing the dynamic range of transmitted X-rays, it is possible to obtain better measurements of transmitted X-ray intensities across the entire viewing field of the image intensifier 180, and thus better tomographic reconstruction.

The attenuator 170 is also formed with calibration steps 175 placed on the outer periphery so as to produce a known specific attenuation (or calibration) with each step, independent of the composition of the core sample 160. The calibration steps 175 can be used to recalibrate each X-ray image to a uniform intensity, thereby mitigating shot-to-shot variations in X-ray source 110 intensity.

Referring now to FIG. 1B, a partial cross sectional view of the optical and shielding components of a typical portable X-ray imaging system 100 is shown. At all points, direct X-ray illumination is shielded from operator exposure to reduce operator exposure levels to or below the regulatory limits set for the particular radiological application. To further explain this shielding, an X-ray shielded volume (comprising the left volume shield 151 and the right volume shield 152) continues from its overlapped slight gap 145 of the telescoping X-ray source shield 140 to the image intensifier 180. In most applications, vendors of X-ray sources 110, X-ray image intensifiers 180, and X-ray imaging devices 190 provide for internal shielding at or exceeding regulatory limits, so that no further additional shielding is necessary. However, for those components not meeting these shielding requirements, further shielding (not shown) is added as required to meet regulatory requirements.

In practice, the imaging system 100 has been reduced in size, and most importantly weight, so as to make the system portable. In one implementation, a long well-bore core, contained within a poly vinyl chloride (PVC) or aluminum tubular covering to prevent core crumbling (not shown), is mounted within the X-ray shielded volume and becomes the core sample 160 to be imaged. The entire X-ray imaging device 100 is vertically translated relative to the sample 160 in order to position for different vertical cross-sectional images, typically with either the X-ray imaging device 100 or the sample 160 remaining vertically stationary. The core sample 160 is rotated as required at each relative vertical position to obtain the number of images necessary for computer aided tomographic (CAT) imaging. By combining rotation of the core sample 160 and relative vertical movement of the imaging device 100, most of the sample 160 can be completely CAT scanned in three dimensions.

Figure 2:
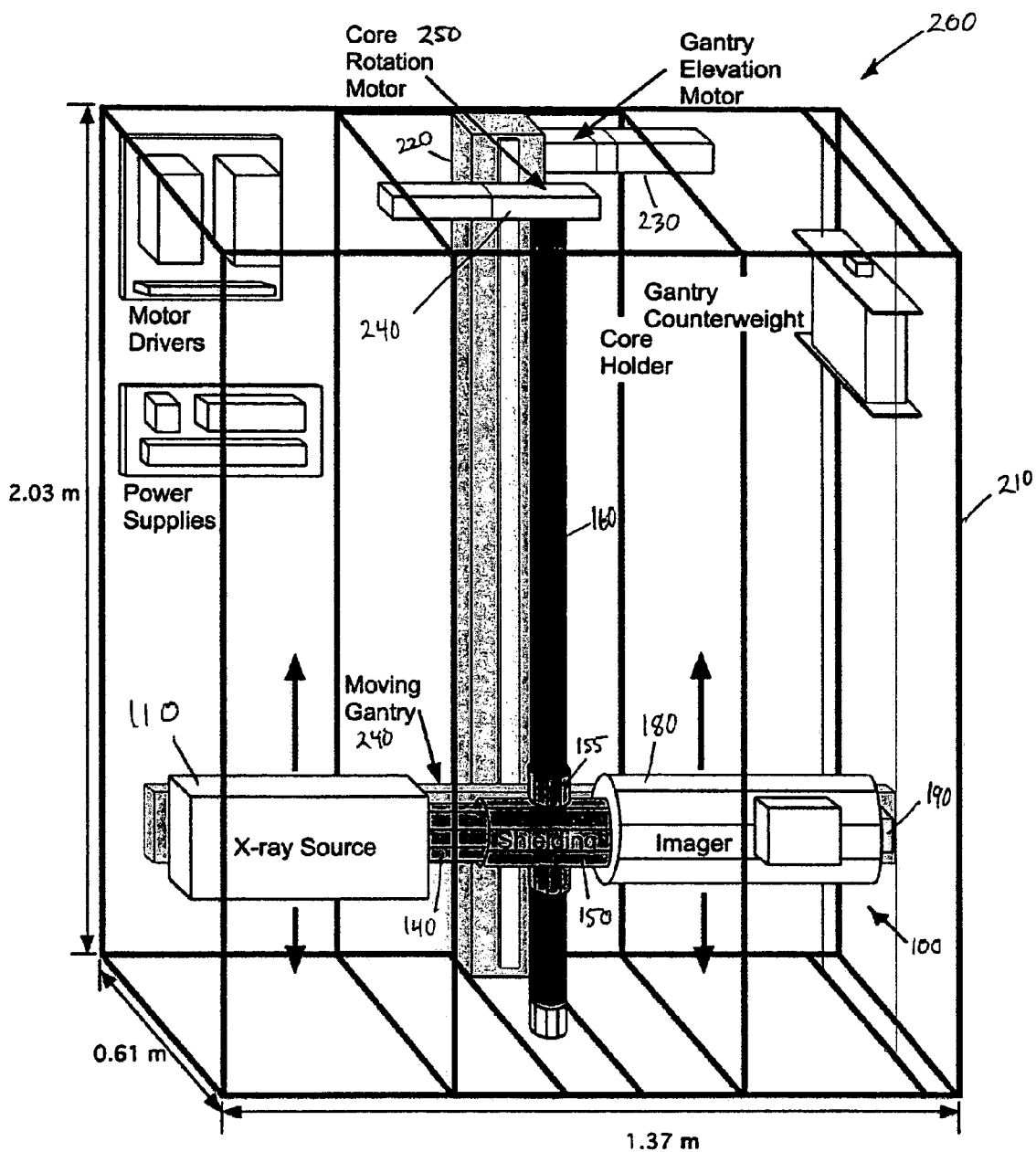
FIG. 2 is a perspective view of the X-ray imaging device with associated movement hardware for scanned, movable operation.

Refer now to FIG. 2, depicting an embodiment of the imaging system 100 installed and operated in portable X-ray imager 200. As a preferred imaging system 100 described above has significant movement relative to a core sample 160, the imaging system 100 is preferably housed in an operator exclusion framework 210, or cabinet, so as to prevent accidental mechanical injury to personnel due to the imaging system 100 movement. This operator exclusion framework 210, unlike the various X-ray shielded components, may be any low weight material contributing to ease of portability, but has no requirement whatsoever for X-ray absorption.

The portable X-ray imager 200 has a vertically mounted gantry ways 220 with a gantry elevation motor 230 providing position control of a movable gantry stage 240 riding upon the gantry ways 220. The gantry elevation motor 230, typically either a stepper motor or DC servomotor with tachometer feedback, actuates the movable gantry stage 240 for controlled vertical translational displacements. The movable gantry stage 240 has mounted to it the imaging system 100. By actuation of the gantry elevation motor 230, the imaging system 100, which is mounted to the gantry stage 240, is made to move vertically relative to the core sample 160.

The core sample 160 is removably attached to a core rotation motor 250, which controllably rotates the core sample 160. The core sample 160 is removably attached to rotational supports at top and bottom that allow rotation controlled by the core rotation motor 250.

By combing vertical translations of the imaging system 100, with step-wise rotational repositionings of the core-sample 160, a series of images may produced. By calibrating each of these images to the attenuator 170 calibration steps 175 (shown previously in FIG. 1B), more uniform intensity X-ray transmission images may be used to create an improved dynamic range tomographic representation of the core sample 160. Using a series of vertically overlapped or adjacent tomographic reconstructions, a contiguous vertical segment of the core sample 160 may be imaged without operator exposure to harmful levels of X-ray radiation.

Recall that methane hydrate outgasses as described previously at standard room temperature and pressure. Therefore, by comparing tomographic scans immediately after the core leaves the well with subsequent scans after complete room temperature disassociation of the methane hydrate, the original concentration and spatial distribution of the methane hydrate may be determined within the core sample 160. By viewing areas of decreased X-ray absorption after outgassing of the methane gas in the core sample 160 by tomographic reconstruction, it is possible to determine the location and percentage composition of the core sample 160 that originally contained methane hydrate.

Equivalents

The description given here, and best modes of operation of the invention, are not intended to limit the scope of the invention. Many modifications, alternative constructions, and equivalents may be employed without departing from the scope and spirit of the invention. Particularly, while a core sample 160 was used to describe the imaging system 100 above, any sample that may be placed within the X-ray shielded volume may be imaged.

Although the implementation of the portable X-ray imager 200 has previously been vertically described, it may also be readily modified for horizontal operation.

All publications, patents, and patent applications mentioned in this specification are herein incorporated by reference to the same extent as if each individual publication or patent application were each specifically and individually indicated to be incorporated by reference.

We claim:

1. An X-ray imaging device for imaging a sample, wherein the sample is within an X-ray shielded volume comprising:

a) an X-ray source capable of emitting an X-ray beam within a beam path to illuminate the sample;
b) a source beam shield connected to the X-ray source;
c) an X-ray detector connected to an exit shield shielding an X-ray beam emerging from the sample;
d) a first volume shield defining an elongated generally convex receptacle for receiving a first portion of the sample, and having therein a transverse elongated shielding portion slidably coupled to said source beam shield; and
e) a second volume shield defining an elongated generally convex receptacle for receiving a second portion of the sample, and having therein a transverse elongated shielding portion slidably coupled to said exit shield;
whereby the sample may extend beyond the first and second volume shields, and whereby these shields may be brought into contacting opposition to provide an x-ray shielded volume containing at least a portion of the sample, the emitted x-ray beam and the emerging x-ray beam.

2. The device of claim 1 wherein said emission from the device is below a regulatory level is at or below 0.5 milliroentgen per hour at any point 5 centimeters outside an external surface of said X-ray imaging device.

3. The device of claim 2 wherein:
a) the sample rotates relative to the X-ray shielded volume.

4. The device of claim 2 further comprising:
a) means for rotating the sample relative to the X-ray shielded volume.

5. The device of claim 4 further comprising:
a) means for translating the sample relative to the X-ray shielded volume.

6. The device of claim 3 wherein:
a) the sample translates relative to the X-ray shielded volume.

7. The device of claim 2 further comprising:
a) a shielded telescoping X-ray source shield permitting elongation of said beam path.

8. An imaging device comprising:
a) a source of ionizing radiation;
b) a detector of ionizing radiation;
c) an attenuator that has calibration steps disposed between the source and detector of ionizing radiation; and
d) a means for shielding an object to be irradiated by said source of ionizing radiation so as to form an image detected by said detector of ionizing radiation;
wherein said means for shielding limits external exposure of ionizing radiation produced by said source of ionizing radiation to a level at or below 0.5 milliroentgen per hour at any point 5 centimeters outside an external surface of said imaging device; and wherein said means for shielding has a mass of less than 200 kg.

9. The imaging device of claim 8 wherein said means for shielding has a mass of less than 14 kg.

10. The imaging device of claim 8 wherein said means for shielding has a mass of less than 10 kg.

11. The imaging device of claim 8 wherein said means for shielding has a mass of less than 8 kg.

12. The imaging device of claim 8 wherein said means for shielding is disposed between said source of ionizing radiation and said detector of ionizing radiation.

13. The imaging device of claim 8 wherein said ionizing radiation is an X-ray.

14. The imaging device of claim 13 wherein said X-ray has an energy selected from the group comprising: 10–130 kV, 20–130 kV, and 70–80 kV.

15. The imaging device of claim 13 wherein said X-ray has a wavelength between about $10^{-5}$ to $10^3$ Å.

16. The imaging device of claim 13 wherein said X-ray has a wavelength between about $(10^{-5}-10^3) \times 10^{-10}$ meters.

17. An X-ray imaging device for imaging a sample contained within an X-ray shielded volume comprising:
 a) an X-ray source;
 b) an X-ray imaging detector comprising:
  i) an X-ray image intensifier, and
  ii) an image detector that detects the output of said X-ray image intensifier; and
 c) an X-ray shielded volume comprising:
  i) a core volume shielded by a left volume shield and a right volume shield separably connected so as to permit insertion and removal of a sample, said core volume having a top opening and a bottom opening,
  ii) a beam path emitted from said X-ray source within a beam path volume,
  iii) a shielded telescoping sleeve permitting elongation of said beam path volume,
  iv) said beam path volume intersecting said core volume;
  v) wherein said X-ray source is located at one end of said beam path, and said X-ray imaging detector is located at another end of said beam path so as to image an object placed in said beam path; and
 d) wherein said X-ray source is shielded from external radiation by said X-ray shielded volume.

18. The device of claim 17 wherein:
 a) the sample rotates relative to the core volume.

19. The device of claim 17 wherein:
 a) the sample translates relative to the core volume moving in the top opening and the bottom opening.

20. The device of claim 17 wherein:
 a) the sample rotates relative to the core volume, and b) the sample translates relative to the core volume moving in the top opening and the bottom opening.

21. The device of claim 17 wherein X-ray emissions are at or below 0.5 milliroentgen per hour at any point 5 centimeters outside an external surface of said X-ray imaging device.

22. The device of claim 17 wherein the mass of said X-ray shielded volume is less than 14 kg.

23. The device of claim 17 wherein the mass of said X-ray shielded volume is less than 10 kg.

24. The device of claim 17 wherein the mass of said X-ray shielded volume is less than 8 kg.

25. The device of claim 17 wherein the mass of said X-ray shielded volume is less than 5 kg.

26. The device of claim 17 wherein said X-ray shielded volume X-ray shields at said top and bottom openings.

27. The device of claim 26 wherein said X-ray shielded volume further comprises a rotatable stage within said X-ray shielded volume for controlled rotation of said sample.

28. A portable imaging device for imaging a sample contained within a shielded volume comprising:
 a) a penetrative photon source;
 b) a penetrative photon imaging detector comprising:
  i) a penetrative photon image intensifier, and
  ii) an penetrative photon image detector that detects the output of said penetrative photon image intensifier; and
 c) an penetrative photon shielded volume comprising:
  i) a core volume shielded by a left volume shield and a right volume shield separably connected so as to permit insertion and removal of a sample, said core volume having a top opening and a bottom opening,
  ii) a penetrative photon beam path emitted within a beam path volume,
  iii) a shielded telescoping sleeve permitting elongation of said beam path volume,
  iv) said beam path volume intersecting said core volume;
  v) wherein said penetrative photon source is located at one end of said beam path, and said penetrative photon imaging detector is located at another end of said beam path so as to image an object placed in said beam path; and
 d) wherein said penetrative photon source is substantially shielded from external radiation by said penetrative photon shielded volume.

29. A portable imaging device for imaging a sample contained within a shielded volume comprising:
 a) means for generating penetrative photons for imaging a sample;
 b) means for detecting penetrative photons transmitted through said sample and creating an image, wherein said means for detecting penetrative photons comprises:
  i) an X-ray image intensifier;
  ii) an attenuator that has calibration steps disposed between the generating means and the X-ray image intensifier; and
 c) means for shielding said penetrative photons to a level below 0.5 milliroentgen per hour at any point 5 centimeters outside an external surface of said portable imaging device.

30. The portable imaging device of claim 29 further comprising:
 a) means for telescoping said generating means closer and further away from said detecting means.

31. The portable imaging device of claim 29 further comprising:
 a) means for mechanically protecting personnel from movements of said portable imaging device.

32. The portable imaging device of claim 29 further comprising:
 a) means for translating and rotating said sample relative to said portable imaging device.

33. A method for using the portable imaging device of claim 29 to image said sample inserted within said portable imaging device, the method comprising:
 a) imaging a first segment of said sample using said penetrative photons to create images;
 b) rotating said sample to create multiple images;
 c) assembling a first three dimensional representation of said sample first segment;
 d) translating said sample to a next segment to create a next three dimensional representation; and
 e) repeating the above steps until some or all of the sample has been imaged.

* * * * *

UNITED STATES PATENT AND TRADEMARK OFFICE
CERTIFICATE OF CORRECTION

PATENT NO.         : 7,082,185 B2                                      Page 1 of 1
APPLICATION NO. : 10/777947
DATED              : July 25, 2006
INVENTOR(S)        : Barry M. Freifeld et al.

It is certified that error appears in the above-identified patent and that said Letters Patent is hereby corrected as shown below:

Please delete item [75], inventors name "Timothy J. Kneafaley" should be -- Timothy J. Kneafsey --.

Signed and Sealed this

Seventeenth Day of October, 2006

JON W. DUDAS
*Director of the United States Patent and Trademark Office*